(12) United States Patent
Bader

(10) Patent No.: US 7,704,734 B2
(45) Date of Patent: Apr. 27, 2010

(54) DEVICE FOR RAISING OR CULTIVATING CELLS IN A CONTAINER-LIKE RECEPTACLE

(76) Inventor: Augustinus Bader, Krankenhausstr. 7, D-04668 Parthenstein-Klinga (DE)

(*) Notice: Subject to any disclaimer, the term of this patent is extended or adjusted under 35 U.S.C. 154(b) by 866 days.

(21) Appl. No.: 10/501,447

(22) PCT Filed: Jan. 11, 2003

(86) PCT No.: PCT/EP03/00211

§ 371 (c)(1),
(2), (4) Date: Sep. 2, 2004

(87) PCT Pub. No.: WO03/060055

PCT Pub. Date: Jul. 24, 2003

(65) Prior Publication Data

US 2005/0084954 A1    Apr. 21, 2005

(30) Foreign Application Priority Data

Jan. 15, 2002 (DE) .................. 102 01 259

(51) Int. Cl.
  *C12M 1/00* (2006.01)
  *C12M 3/00* (2006.01)
(52) U.S. Cl. .................................. 435/293.1
(58) Field of Classification Search .......... 435/295.1, 435/304.3, 293.1, 395, 1.1, 299.1, 303.1, 435/304.1
See application file for complete search history.

(56) References Cited

U.S. PATENT DOCUMENTS

| | | | |
|---|---|---|---|
| 1,337,981 A * | 4/1920 | Waggoner | ................... 220/314 |
| 2,701,229 A | 2/1955 | Scherr | |
| 4,377,639 A * | 3/1983 | Lee | ........................... 435/299.1 |
| 4,412,626 A * | 11/1983 | Gerhard | ....................... 220/1.5 |
| 4,851,354 A * | 7/1989 | Winston et al. | ............. 435/402 |
| 5,005,717 A * | 4/1991 | Oilar | .......................... 215/13.1 |
| 5,215,312 A * | 6/1993 | Knappe et al. | .............. 277/312 |
| 5,219,755 A | 6/1993 | Willemot et al. | |
| 5,267,791 A | 12/1993 | Christian et al. | |
| 5,376,548 A * | 12/1994 | Matsuo et al. | ........... 435/297.2 |
| 5,449,617 A * | 9/1995 | Falkenberg et al. | ......... 435/394 |
| 5,462,874 A * | 10/1995 | Wolf et al. | ................ 435/297.5 |
| 5,705,390 A * | 1/1998 | Kadouri et al. | ............. 435/395 |
| 5,763,279 A * | 6/1998 | Schwarz et al. | ............. 435/383 |
| 5,989,913 A * | 11/1999 | Anderson et al. | ........... 435/394 |
| 6,071,088 A * | 6/2000 | Bishop et al. | ............... 417/322 |

(Continued)

FOREIGN PATENT DOCUMENTS

DE        196 31 997 A1    2/1998

(Continued)

OTHER PUBLICATIONS

U.S. Appl. No. 60/342,992, filed Dec. 2001, DiMilla et al.*

*Primary Examiner*—Walter D Griffin
*Assistant Examiner*—Shanta G Doe
(74) *Attorney, Agent, or Firm*—Davis & Bujold, P.L.L.C.

(57) ABSTRACT

A device for raising or cultivating cells in a container-like receptacle, comprises a base and at least one lid. The at least one lid is connected to the receptacle in a pressure-tight manner. The receptacle or the lid is provided with at least one connector drilling for the introduction and/or extraction of culture medium and/or oxygen.

17 Claims, 7 Drawing Sheets

U.S. PATENT DOCUMENTS

| | | |
|---|---|---|
| 6,855,542 B2 * | 2/2005 | DiMilla et al. ............ 435/289.1 |
| 7,144,726 B2 * | 12/2006 | Takagi et al. ............. 435/286.6 |
| 2002/0106625 A1 * | 8/2002 | Hung et al. .................. 435/1.1 |
| 2003/0186217 A1 | 10/2003 | Bader |
| 2004/0020889 A1 * | 2/2004 | Willemsen ................. 215/230 |

FOREIGN PATENT DOCUMENTS

| | | | |
|---|---|---|---|
| DE | 197 10 650 A1 | 9/1998 | |
| GB | 2 305 936 A | 4/1997 | |
| JP | 06343457 | 12/1994 | |
| JP | 08154663 | 6/1996 | |
| JP | 2000078963 | * | 3/2000 |
| WO | WO-02/24861 A2 | 3/2002 | |

* cited by examiner

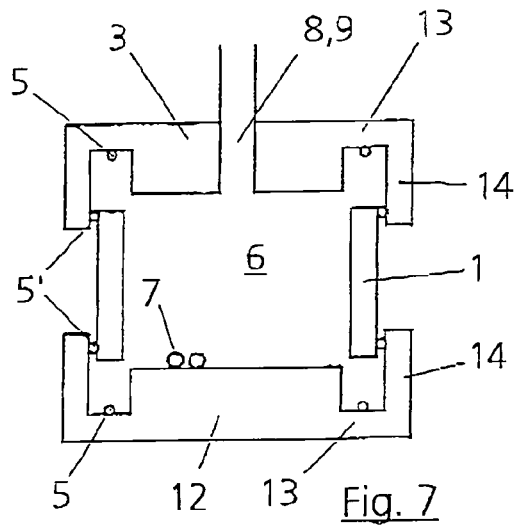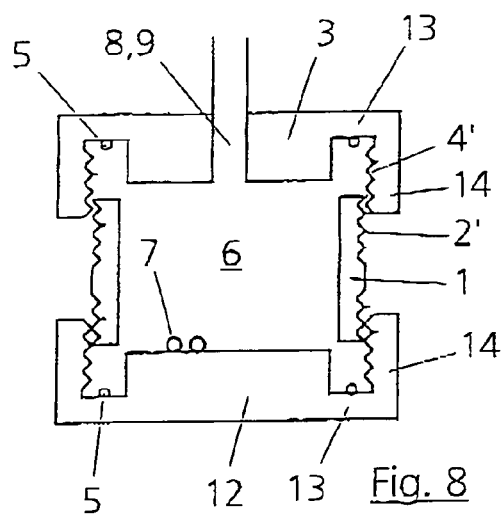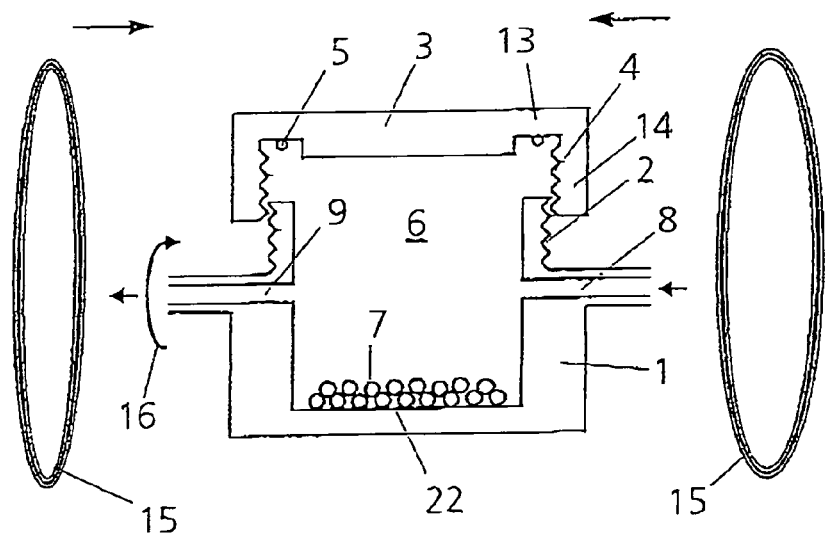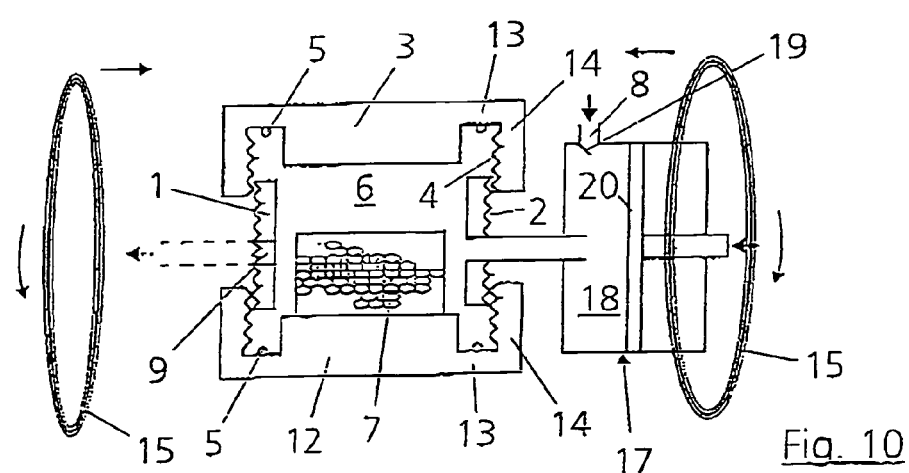

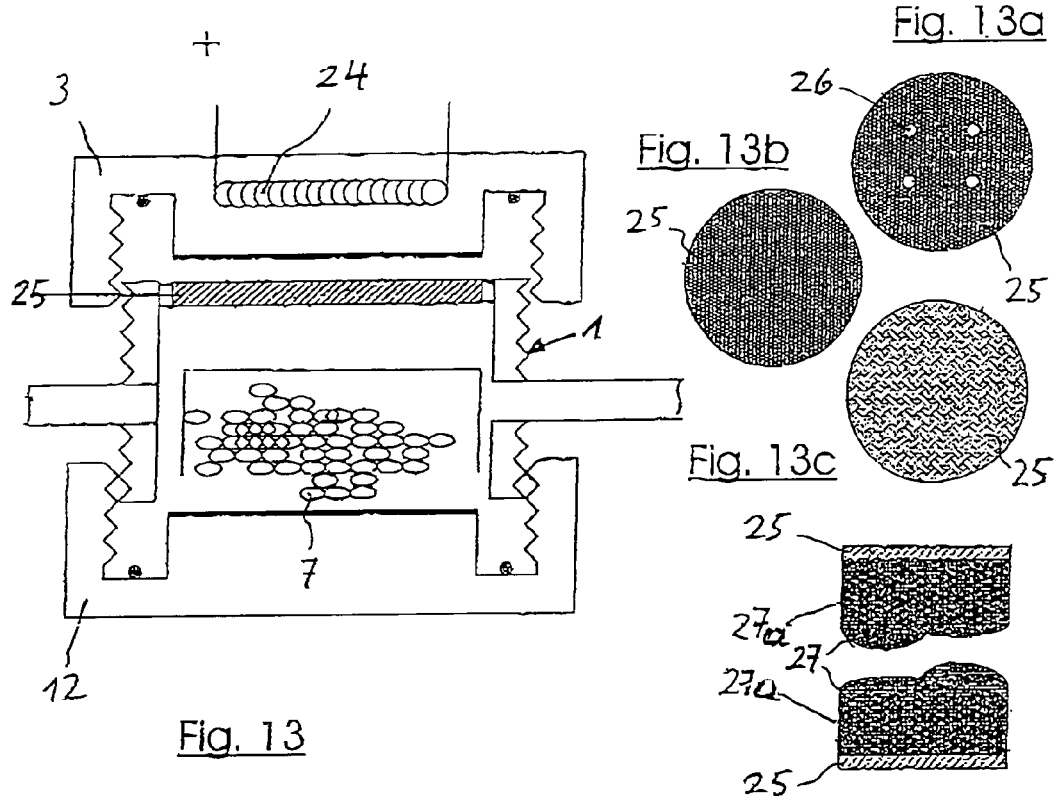
Fig. 13a
Fig. 13b
Fig. 13
Fig. 13c
Fig. 13d
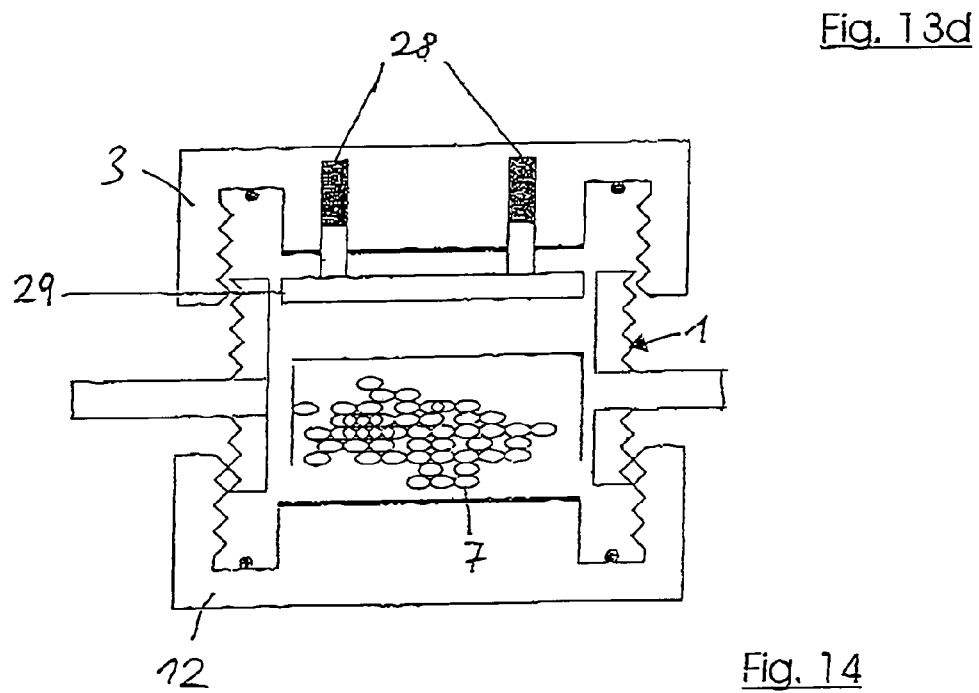
Fig. 14

DEVICE FOR RAISING OR CULTIVATING CELLS IN A CONTAINER-LIKE RECEPTACLE

This application is a national stage completion of PCT/EP2003/000211 filed Jan. 11, 2003 which claims priority from German application Serial No. 102 01 259.8 filed Jan. 15, 2002.

FIELD OF THE INVENTION

The invention relates to a device for raising or cultivating cells in a container-like receptacle with comprises a base and at least one lid.

BACKGROUND OF THE INVENTION

For laboratory requirements, it is known to raise or cultivate cell cultures in a shallow receptacle or dish, the cells simply being placed in the receptacle and culture medium being added. A lid is then placed on the receptacle.

A disadvantage is that this method can only be used for small quantities. In particular, the known system is not suitable for cultivating or raising cells in batches. Moreover, it is impossible to achieve in vivo conditions, and sterility is not guaranteed.

An alternative to this was to use a closed system which comprised a receptacle with a lid or closure piece and which permitted sterility. However, a disadvantage of this was that removing the cell culture was very laborious and time-consuming.

It is therefore an object of the present invention to improve a device of the type mentioned at the outset in such a way that it can be used in a highly versatile manner for raising or cultivating cells, particularly in large-scale operations, the aim being to achieve as far as possible in vivo conditions and sterility. Moreover, after they have been cultivated, the cell cultures should be able to be removed from the receptacle without great effort and without being damaged.

SUMMARY OF THE INVENTION

According to the invention, this object is achieved by the features in the characterizing part of claim 1.

In the device according to the invention, the cells in the receptacle are no longer "left to themselves", and instead an active process takes place in practice. On the one hand, culture medium can be introduced continuously or intermittently, and, on the other hand, it is possible for the cell cultures forming to be acted upon with pressure. This pressure actuation can even be effected with alternating pressure in order to simulate natural conditions as far as possible.

The cells can be raised or cultivated as separate cell cultures. In the same way they can also be formed on structures in order to produce implants.

In the receptacle according to the invention, the cells can in this way also be exposed to shearing forces or pressure forces. With the device according to the invention, a wide variety of cell cultures can be raised or cultivated in a highly versatile manner.

The receptacle itself can also be provided for this purpose variously with one or two lids. Likewise, a common connector bore can be provided for the introduction of culture medium and for its return. Of course, separate connector bores are also possible, in which case parallel flows or through-flows are possible depending on the arrangement of the connector bores.

By virtue of the configuration according to the invention with one or two lids or a lid and base, and between them a receptacle which can simply be a cylinder open at the top and bottom, the cell cultures can easily be removed from the receptacle, after they have been treated or raised, without great effort and without damaging them.

Since according to the invention the cells are raised or cultivated on the lower lid or base or also under the upper lid, e.g. on a frame connected to the upper lid, the cell cultures can be easily removed from the receptacle once they are ready. In any event, good accessibility is afforded by the removable lids or base.

For pressurization, the receptacle, e.g. the circumferential wall of the cylindrical receptacle, can also be made elastic.

The connector bore or connector bores can be arranged in one lid or, if two lids are present, in both lids. Likewise, it is also possible to form the connector bores in the cylindrical middle part. The number and arrangement of the connector bores depends on the application and on the cells which are to be raised or cultivated.

For a tight connection between the lid or lids and the receptacle, clamp connections, sealing rings or threaded connections with internal and external threads can be provided.

Very good sealing conditions and thus pressure conditions are obtained if the lid or lids are provided with extension rings which then sealingly enclose the cylindrical middle part of the receptacle from the outside.

If the device according to the invention is to be subjected to a rolling or turning movement, tensioning rings can be fitted laterally onto the device, which tensioning rings grip the lid or lids and the receptacle, and a turning or rolling means can then be applied to them.

A wide variety of pressurizing means can be used to subject the interior of the receptacle forming the cell culture chamber to pressure. Suitable for this purpose are, for example, cylinder/piston units which can also operate in pulsed mode for alternating pressure loads.

If necessary, the receptacle can also be designed as a two-chamber system so that two different cells or two identical cells can be cultivated or raised separate from one another.

In this case, it is advantageous if the lid of the receptacle is provided with a suspension means on which a platform for receiving cells is arranged. In this way, one cell type is raised on the platform, while another cell type can be cultivated on the base of the receptacle.

If necessary, the receptacle or the cylindrical circumferential wall of the receptacle can be made porous or gas-permeable, so that in this way too culture medium and/or a gaseous medium, for example air or oxygen, can be delivered from this side.

BRIEF DESCRIPTION OF THE DRAWINGS

The invention will now be described, by way of example, with reference to the accompanying drawing in which:

FIG. 7 shows a similar configuration to the one in FIG. 6, with a clamp connection;

FIG. 8 shows a similar configuration to the one in FIGS. 6 and 7, with threaded connections;

FIG. 9 shows an embodiment with two lateral tensioning rings;

FIG. 10 shows an embodiment similar to the embodiment in FIG. 9, with a pressurizing means;

FIG. 13 shows a configuration with a pressure force generated by magnetic forces;

FIGS. 13a, 13b and 13c show different pressure disk profiles;

FIG. 13d shows a mineral matrix for bone replacement as support structure with two pressure disks;

FIG. 14 shows a configuration with expandable elements for generating pressure forces;

DETAILED DESCRIPTION OF THE INVENTION

Figure 1:
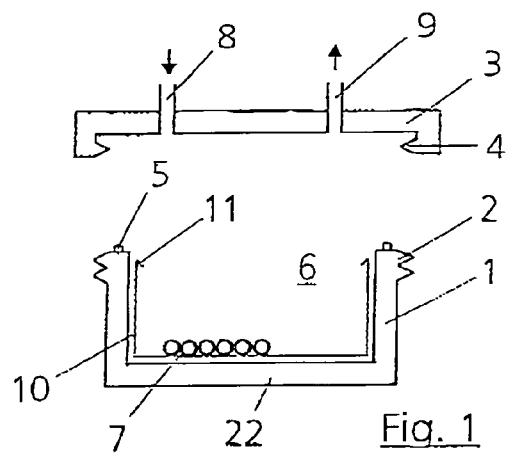
FIG. 1 shows a cross section through a first embodiment of a device with a receptacle and a lid.

According to the illustrative embodiment in FIG. 1, which shows the basic configuration of the device according to the invention, a receptacle 1 is provided which has an external thread 2. A lid 3 with an internal thread 4 is screwed onto the receptacle 1, and a sealing ring 5 forms a pressure-tight closure of a cell culture chamber 6 for cells 7 provided in the interior of the receptacle 1.

The lid 3 is provided with an inlet connector bore 8 and an outlet connector bore 9 in order to introduce culture medium and if appropriate also oxygen into the cell culture chamber 6 via corresponding lines or tubes.

For easier handling, a tray 10 can be inserted into the receptacle 1 so as to make it easier to insert and remove the cells 7 which are to be cultivated or raised. For this purpose, beads, flanges 11 or the like which are provided in the upper area of the tray 10 can also serve for easier removal and easier insertion. The tray 10 shown only in FIG. 1 can of course also be provided in the same way or in a similar way in the other illustrative embodiments.

Figure 2:
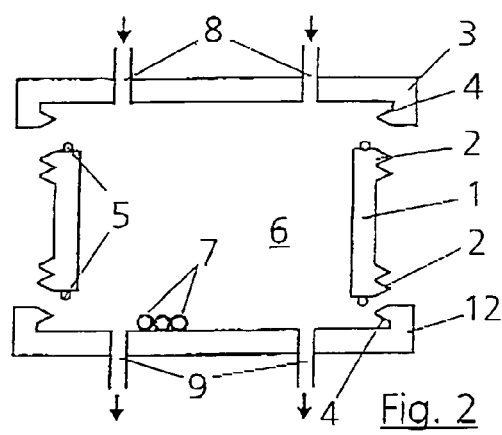
FIG. 2 shows a cross section through a device with a cylindrical middle part and an upper lid and lower lid.

FIG. 2 shows a configuration where the receptacle 1 forms a cylindrical middle part which can be closed with the upper lid 3 in the same way as in the illustrative embodiment according to FIG. 1. Provided on the underside there is a further, lower lid 12 which forms the base of the receptacle and which likewise has an internal thread 4 which interacts with the external thread 2 of the middle part, said middle part in this case being provided with two external threads 2, unless one continuous thread is present. As will also be apparent from FIG. 2, inlet and outlet connector bores 8 and 9 are provided in both lids 3 and 12.

Figure 3:
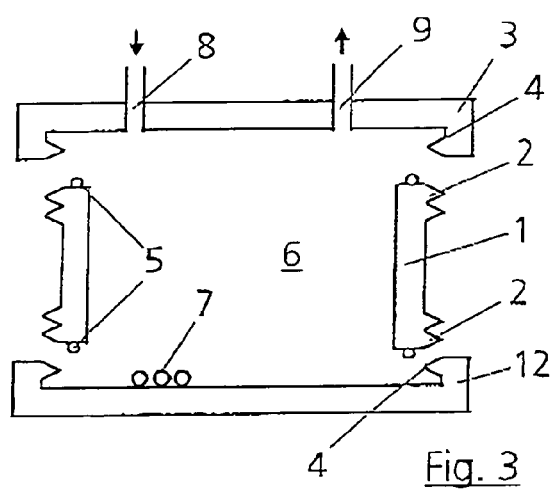
FIG. 3 shows a similar configuration to the one in FIG. 2, with an inlet connector and an outlet connector being arranged in the upper lid.

FIG. 3 shows a similar configuration to the one in FIG. 2, with an inlet connector bore 8 and an outlet connector bore 9 being arranged only in the upper lid 3. In the same way as in the illustrative embodiment according to FIG. 2, sealing rings 5 are provided on both ends of the cylindrical middle part of the receptacle 1.

Figure 4:
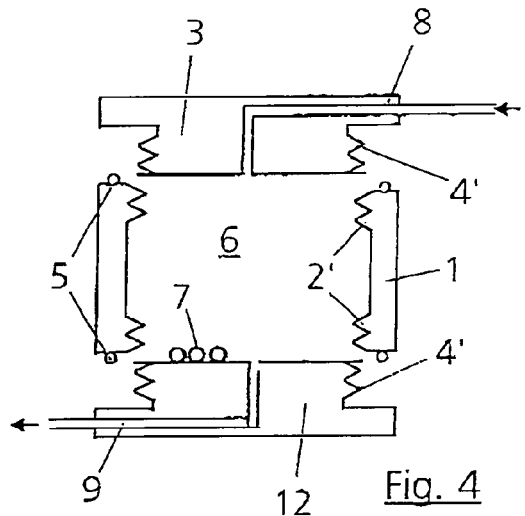
FIG. 4 shows a further embodiment of the device according to the invention.

FIG. 4 shows an embodiment in which the cylindrical middle part as receptacle 1 is provided with an internal thread 2' which cooperates with an external thread 4' of the upper lid 3 and of the lower lid 12. Here too, sealing rings 5 are provided on both ends of the receptacle 1. In this case, an inlet connector bore 8 is provided in the upper lid 3, and an outlet connector bore 9 is provided in the lower lid 12.

Figure 5:
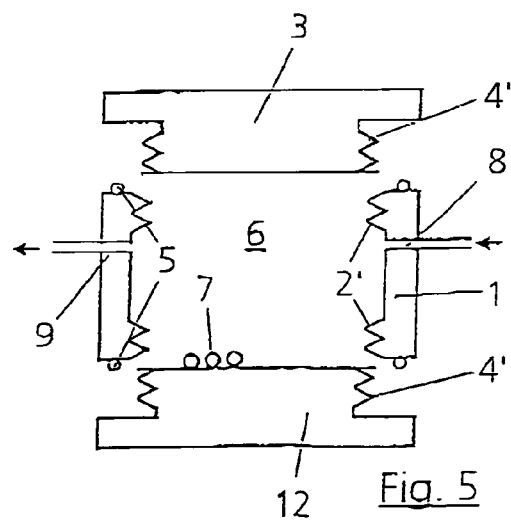
FIG. 5 shows a device according to the invention with an upper lid and a lower lid, each with external thread, and a cylindrical middle part with internal thread.

FIG. 5 shows a similar configuration to FIG. 4. The main difference is simply that the inlet connector bore 8 and the outlet connector bore 9 are arranged opposite one another in the cylindrical middle part of the receptacle 1.

Figure 6:
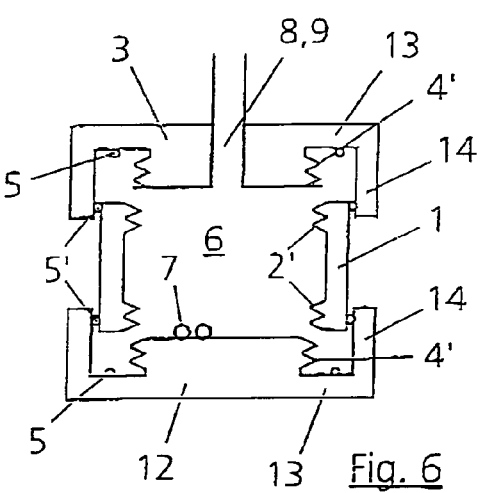
FIG. 6 shows an embodiment with extension rings on an upper lid and a lower lid.

FIG. 6 shows an embodiment with a cylindrical middle part as receptacle 1, an upper lid 3, and a lower lid 12. Both lids 3 and 12 each have an external thread 4' which cooperates with internal threads 2' of the receptacle 1. In addition, both lids 3 and 12 are provided with radial extensions 13 from whose outer ends extension rings 14 extend axially into the receptacle 1, parallel to the longitudinal axis of the receptacle 1. The extension rings 14 enclose the outer wall of the receptacle 1 and, together with additional sealing rings 5', constitute a pressure-tight closure for the cell culture chamber 6. The upper lid 3 is provided with a common connector bore 8, 9 for the introduction and withdrawal of culture medium.

FIG. 7 shows a similar embodiment to the one in FIG. 6. The main difference is simply that, instead of a threaded connection 2', 4', a pressure-tight closure of the cell culture chamber 6 is created by clamp connections between the extension rings 14 and the outside wall of the receptacle 1.

FIG. 8 shows an embodiment similar to those in FIGS. 6 and 7. The main difference here is that the threaded connection between the receptacle 1 and the lids 3 and 12 is formed by internal threads 4' in the extension rings 14, these cooperating with external threads 2' in the receptacle 1.

FIG. 9 shows an embodiment with a receptacle 1 and an upper lid 3, similar to the embodiment according to FIG. 8, but instead of a common connector bore 8, 9 for the introduction and withdrawal of culture medium, an inlet connector bore 8 and an outlet connector bore 9 are arranged in the circumferential wall of the receptacle 1. In addition, FIG. 9 shows two lateral tensioning rings 15 which are pushed round the container-like receptacle 1 and the lid 3 in the arrow direction so that the unit consisting of receptacle 1 and lid 3 can be turned or rolled in arrow direction 16 about the transverse axis with the aid of a turning or rolling means (not shown).

FIG. 10 shows a similar configuration to the one in FIG. 9. In this case, a separate cell culture chamber 6 is formed in the interior of the receptacle 1. Instead of a cell culture chamber 6, it is also possible to provide a structure on which the cells 7 are raised. The separate cell culture chamber 6 or the structure is in this case pressurized via a pressurizing means 17 in the form of a cylinder/piston unit.

The inlet connector bore 8, which can be shut off at the entry point by a check valve 19, opens into a piston chamber 18 of the cylinder/piston unit 17. The culture medium introduced through the inlet connector bore 8 is pressurized by a piston 20 of the cylinder/piston unit 17, and this pressure continues into the interior of the receptacle 1. Culture medium is withdrawn via an outlet connector bore 9 on the side of the receptacle 1 directed away from the inlet. When the interior of the receptacle 1 is to be subjected to an overpressure, which may if appropriate be alternating, the return flow of culture medium will in this case be constricted or the outlet connector bore 9 correspondingly shut off.

Instead of supplying culture medium via the inlet connector bore 8, a separate bore can also be provided for this in one of the two lids 3 or 12 or in the circumferential wall of the receptacle 1. In this case, it is also possible to use gas, e.g. air, to pressurize the interior of the receptacle 1 and thus the cell culture chamber 6.

Figure 11:
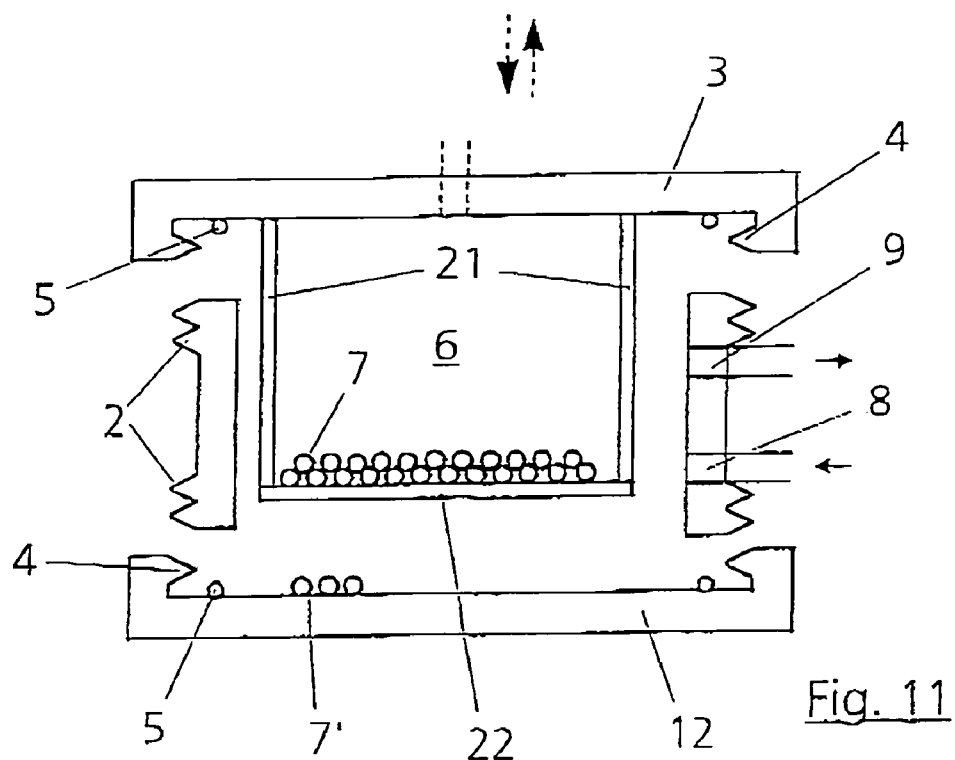
FIG. 11 shows an embodiment with a suspension means in the upper lid, with a cylindrical middle part and a lower lid.

FIG. 11 shows an embodiment with an upper lid 3 and a lower lid 12 and a cylindrical middle part of a receptacle 1. In this case, the upper lid 3 is provided with a suspension means in the form of several rods 21 which are distributed about the circumference and which extend, parallel to the longitudinal axis of the receptacle 1, into the interior of the receptacle 1. Secured at the lower end of the rods 21 there is a platform 22 on which the cells 7 to be cultivated or raised are arranged. The inlet connector bore 8 and the outlet connector bore 9 can each be arranged in the circumferential wall of the receptacle 1. Of course, it is also possible to arrange them in one of the two lids 3 or 12, as is indicated by broken lines. In this case too, separate connector bores are of course also possible for inlet and outlet.

The advantage of the embodiment with the suspension means formed by the rods 21 is that in this way the cells 7 are easier to insert into the receptacle 1 and remove therefrom.

If necessary, the connection of the rods 21 to the platform 22 can be made detachable. Detachability can be achieved, for example, by a clip connection, which also provides for easier handling of the device.

Figure 12:
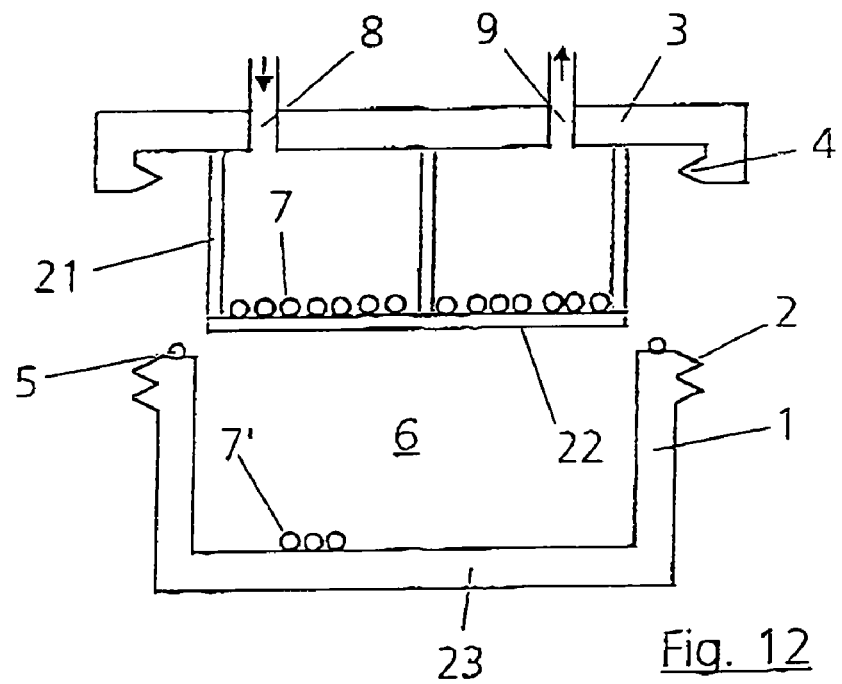
FIG. 12 shows a similar configuration to the one in FIG. 11, in somewhat simpler form with just an upper lid.

FIG. 12 shows an embodiment which is similar to the embodiment shown in FIG. 11. As will be noted, it only has an upper lid 3 and a receptacle 1 with base 23, as is also present in the other embodiments with just one lid 3. The platform 22 in this case is again connected to the upper lid 3 via rods 21.

A further advantage of the embodiments according to FIGS. 11 and 12 is that the receptacle base 23 or inner side of the lid 12 provides an additional possibility for raising or cultivating cells 7. In this way, a two-chamber system for cultivation of two cell cultures is created.

Instead of inlet connector bores 8 and outlet connector bores 9 for culture medium, culture medium can of course also be introduced continuously into the receptacle 1, and the inlet connector bores 8 and outlet connector bores 9 then serve only for oxygen supply.

Alternatively, it is also possible to provide separate connector bores for oxygen and culture medium.

The platform 22 can be designed as a solid unit. Alternatively, it is also possible for this purpose to provide a membrane, e.g. a porous membrane, which allows oxygen to pass through.

FIGS. 13 through 20 show further configurations of the invention, the basic structure of the device with receptacle 1 and both lids 3, 12 and/or base 23 having been retained, for which reason, to keep matters simple, only the relevant reference numbers have been repeated in the following description of these figures.

FIG. 13 shows a receptacle 1 in which a magnetic means 24, e.g. a magnet coil through which current flows, is incorporated in the area of the upper lid 3. Under the magnetic means 24 there is a magnetizable pressure disk 25 which is connected elastically to the receptacle 1 in a manner not shown in detail.

Through a movement of the pressure disk 25 caused by activation of the magnetic means 24, generated by alternate current directions for example, an internal pressure load is exerted on the cells 7.

FIG. 13a shows a plan view of the profile of a pressure disk 25, small openings 26 being provided so that culture medium located in the inside of the receptacle 1 can pass through.

FIGS. 13b and 13c show alternative pressure disks 25 in the form of a mesh structure or grid structure so that culture medium can pass through.

Of course, the magnet coil acting as magnetic means 24 can also be arranged outside the lid 3, above the latter. In this configuration, the lid 3 of course has to be made of nonmagnetizable material, e.g. plastic. In this case, suitably large magnetic means 24 can be provided and correspondingly high pressure forces generated.

FIG. 13d shows a configuration of an implant, cartilage profiles 27 being arranged on a mineral matrix for bone replacement as support structure 27a. Here, two support structures are provided which are arranged one above the other and on each of which a pressure disk 25 is arranged. The mineral matrix can, for example, be a bone structure, e.g. of calcium phosphate.

The mineral matrix can also have other profiles as are required for implants, e.g. joint structures. It is also possible, of course, to deviate from the circular shape. The same also applies in principle to the receptacle 1.

FIG. 14 shows a configuration with expandable elements 28 which axially displace a plate 29 arranged movably in the receptacle 1 or the lid 3, in the same way as the pressure disks 25, and thus can exert alternating pressure forces on the cells 7. The expandable elements used can, for example, be shape-memory metals or plastics which deform and then return to the original shape. Thus, for example, there are also plastics which can expand through electrical change. Elements with shape-memory function react, for example, to certain temperatures or to ultrasound and in this way alter their state, thus generating a movement of the plate 30. Spring devices are also possible, as are motors with accumulators or batteries.

Figure 15:
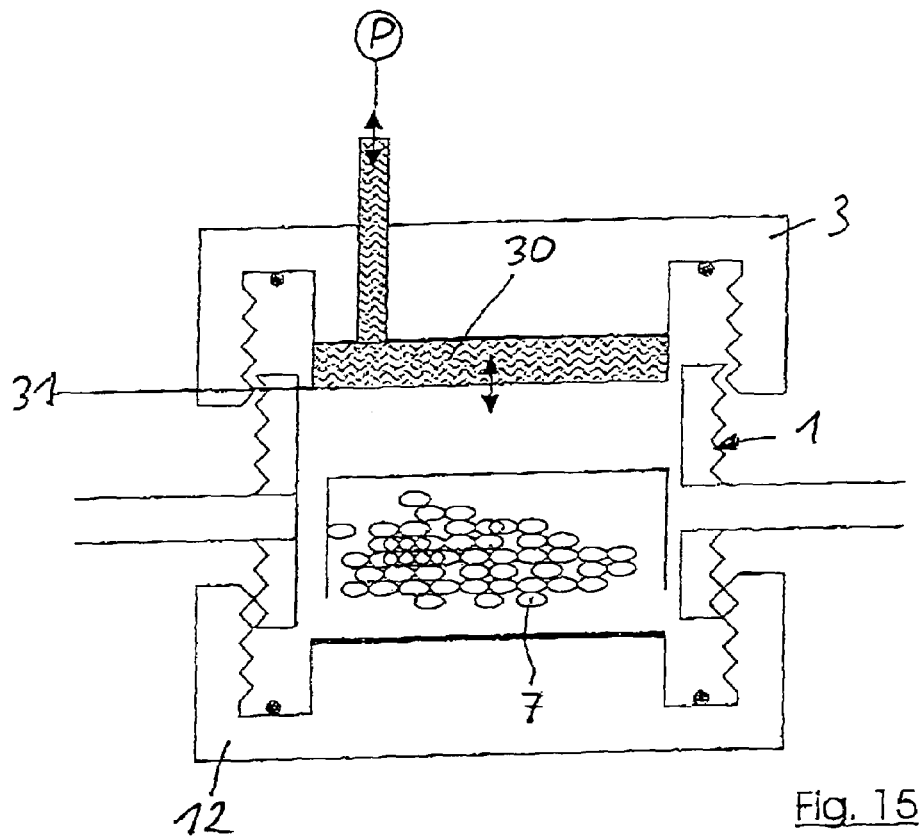
FIG. 15 shows a configuration with hydraulic or pneumatic elements for generating pressure forces.

FIG. 15 likewise shows internal pressurization of cells 7 by a hydraulic or pneumatic means 30 arranged in the receptacle 1 or in the lid 3. As will be noted, the means 30 has a movable film, plate or membrane 31, behind which a hydraulic liquid or a gas acting as fluid is located. The hydraulic liquid or the gaseous medium is subjected to alternating pressure by a pressurizing means P (not shown in detail), as a result of which alternating pressure loads are exerted on the cells 7. Instead of an elastic plate or membrane 31, a balloon can also be used, if required, in order to obtain the possibility of greater variation. For example, all the walls of the receptacle can be covered on the inner side by such a bag or balloon, in which case the implant or cell cultures are located in the inside. In this way, an alternating pressure load is exerted all round from outside.

Figure 16:
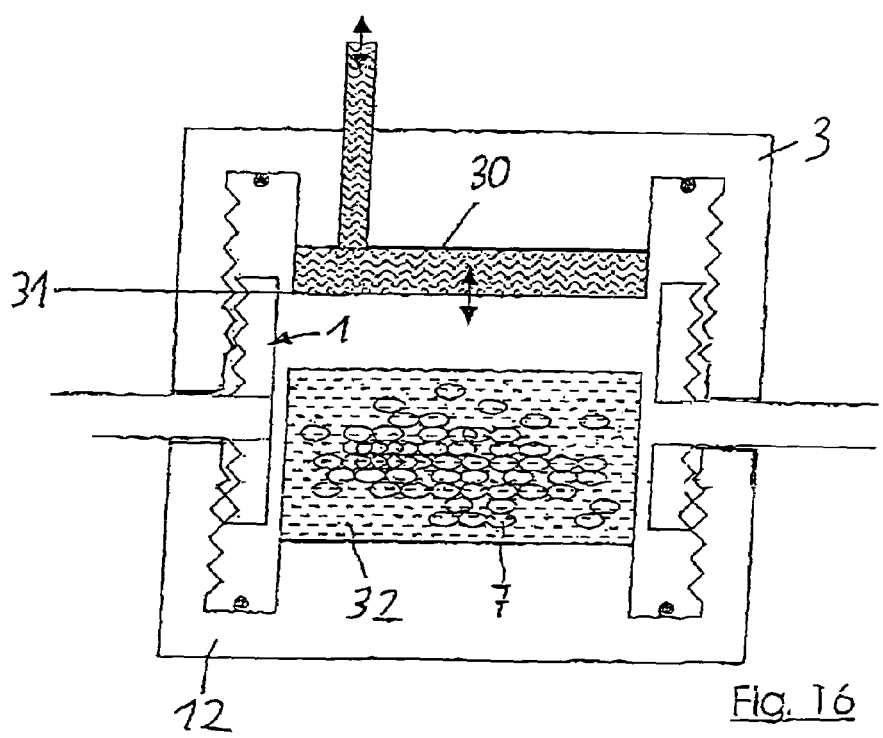
FIG. 16 shows a similar configuration to the one in FIG. 15.

FIG. 16 shows a similar configuration in which the cells 7 lie in a gel 32.

Figure 17:
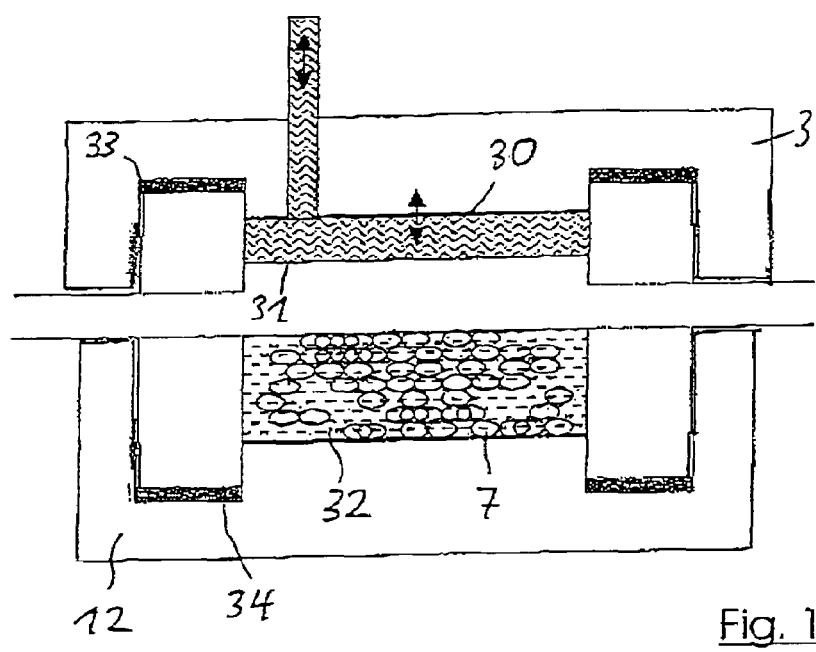
FIG. 17 shows a further configuration similar to those in FIGS. 15 and 16.

FIG. 17 likewise shows a similar configuration to the one in FIG. 16, the sealing between the upper lid 3 and the lower lid 12 being obtained by sealing rings 33 and 34.

Figure 18:
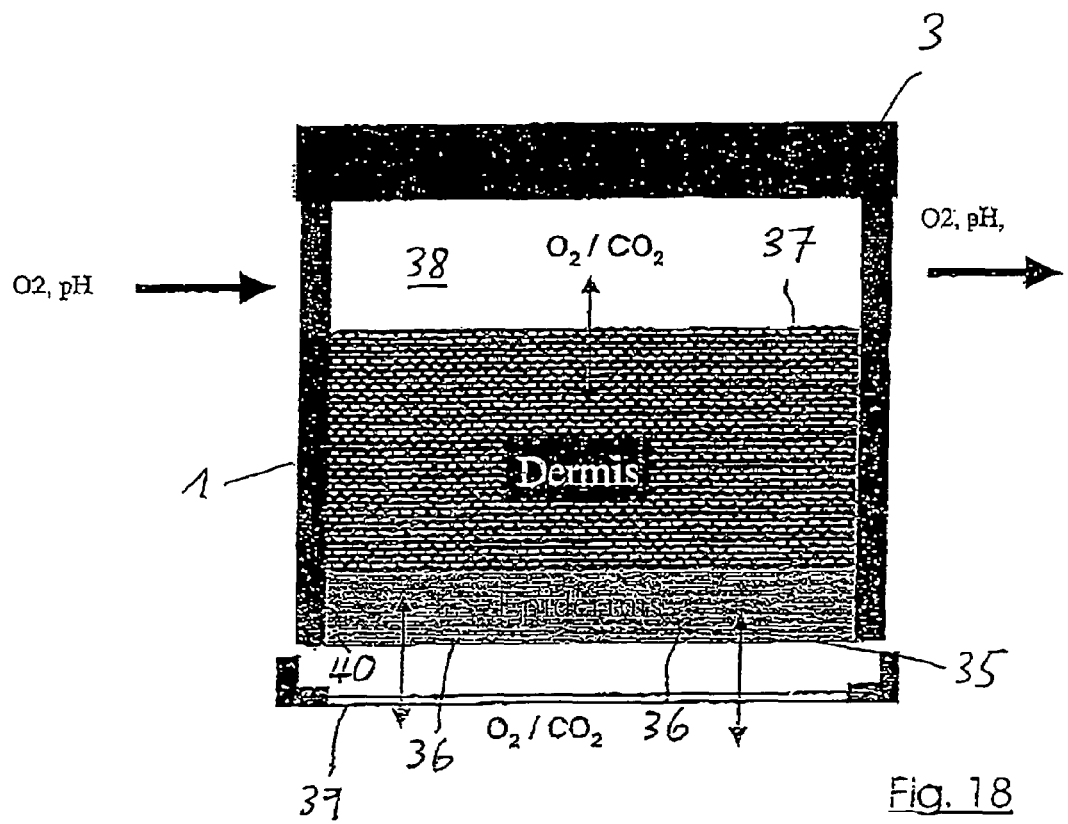
FIG. 18 shows a configuration with a gas-permeable membrane as base.

FIG. 18 shows a configuration in which the base of the receptacle is formed by a gas-permeable membrane 35, e.g. of PTFE or silicone. The important thing is that oxygen can pass into the receptacle 1 through the membrane 35. In this configuration too, an implant growing in the interior of the receptacle can be easily removed. Such a configuration is suitable, for example, for growing epidermis 36, i.e. the top layer of the skin, on the membrane 35. The cells are supplied with air through the gas-permeable membrane 35. The aim here is to have the cells grow from the underside upward. In addition, a dermis 37 is then applied on top, the cells being arranged or cast in a collagen structure or in fibrin. At the top, above the dermis 37, there is a clean area 38 in which air, oxygen and/or carbon dioxide is introduced. Pressurization is also possible here.

In this way, a skin structure is obtained as exists in reality. If so required, various other cells can also be added, for example endothelial cells in order to achieve vascularization on the top face.

To achieve sterility and protection for the membrane 35, a covering structure 39 can, if required, be fitted tightly or screwed on at the bottom.

On the inside, the receptacle can be provided with a peel-off film 40 for transplantations. On completion of the cell cultivation, the covering structure 39 is in this case removed and the film 40 is then peeled off like a plaster. In this way, the implant can be easily removed and then used. The dermis 37 then lies in the correct position on the wound and, when the film is peeled off, the epidermis 36 lies on top.

Instead of a covering structure 39, a chamber with lateral openings can also be provided, in which case a sterile filter is fitted.

Figure 19:
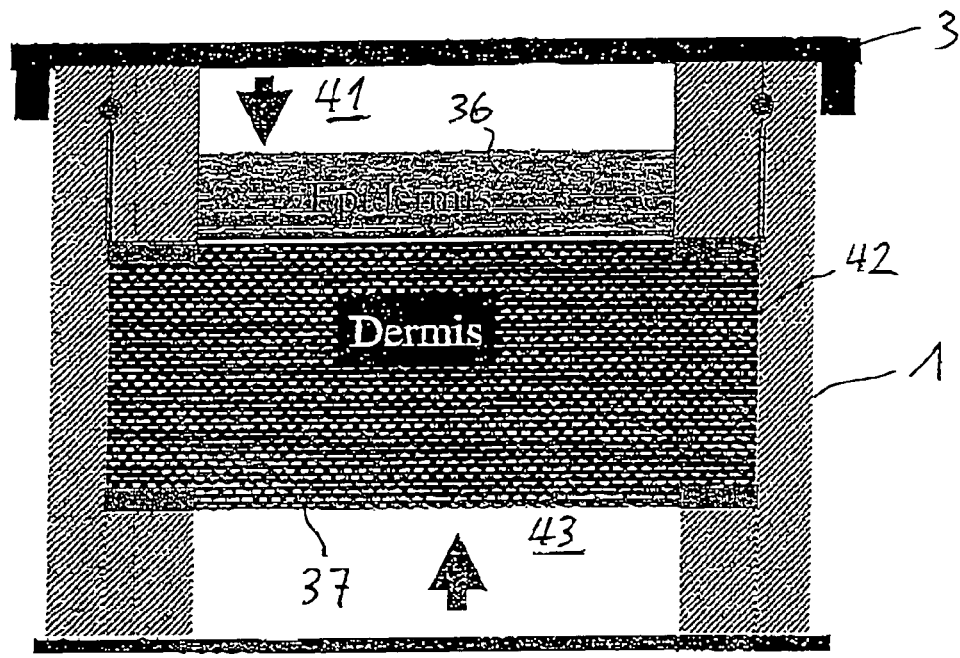
FIG. 19 shows a configuration with a three-chamber system.
Figure 20:
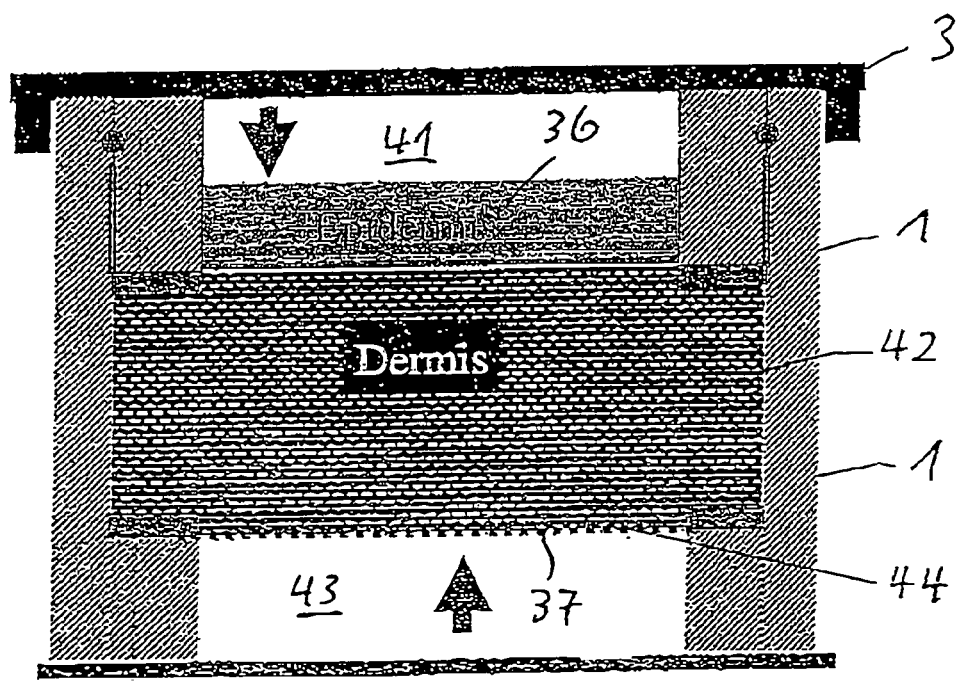
FIG. 20 shows a similar configuration to the one in FIG. 19.

FIG. 19 shows a similar configuration to the one in FIG. 18. Here, by contrast, a multi-chamber system is formed, with an upper chamber 41, a middle chamber 42 and a lower chamber 43. Separate inlets and outlets can be provided for all three chambers 41, 42, 43. Thus, for example, the epidermis 36 can be arranged in the chamber 41, the dermis 38 can be arranged in the chamber 42, and the lower chamber 43 is used for the supply of air or oxygen. Culture medium can be introduced into the chamber 41 in a first step. Then, in a second phase after the cells 7 have grown, if differentiation is desired, oxygen or air can be introduced into the chamber 41 so that the epidermis cells 36 acquire a dry environment and are then able to dry out and keratinize. In this way, the upper layer of skin is then formed. If one then wishes to implant the whole arrangement, the receptacle can be easily opened and the implant removed.

If the cells 7 arranged in the chamber 42 require a support structure, a porous support or membrane 44 can be provided on the underside and constitutes the division between the chamber 42 and the chamber 43.

The invention claimed is:

1. A device for raising or cultivating cells in a container-like receptacle (1), the device comprising:
a cylindrical middle part of the device being closed off at a top by an upper lid (3) and a lower lid (12) which forms a base of the receptacle (1),
wherein the upper lid (3) and the lower lid (12) are connected to the middle part in a pressure-tight manner and the upper lid (3) and the lower lid (12) are each provided with at least one inlet bore (8) for one of an introduction and a withdrawal of a culture medium and oxygen,
the upper and the lower lids (3, 12) and the middle part are connected to one another by mating internal and external threaded connections (2, 4), and each threaded connection is provided with at least one sealing ring, and
the upper lid (3) and the lower lid (12) each include an extension ring (14) having an extension ring region extending beyond the threaded connections (2, 4) to at least partially enclose the cylindrical middle part and each extension ring region including at least one sealing ring located between the middle part and the extension ring region to additionally seal the middle part.

2. A device for raising or cultivating cells in a container-like receptacle which comprises:
a base receptacle (1); and
at least an upper lid (3);
wherein the upper lid (3) is connected to the base receptacle (1) in a pressure-tight manner by mating internal and external threaded connections of the upper lid (3) and base receptacle (1), and each threaded connection is provided with at least one sealing ring, and at least one of the base receptacle (1) and the upper lid (3) is provided with at least one inlet bore (8) for one of introduction and withdrawal of a culture medium and oxygen;
at least one resilient lateral tensioning ring (15) encircles both an exterior surface of the base receptacle (1) and an exterior surface of the upper lid (3) to retain the upper lid (3) in sealing engagement with the base receptacle (1) when the container-like receptacle is rotated about a transverse axis; and
a pressurizing device coupled to the device for raising or cultivating cells for exerting pressure on the cells (7) being cultivated within the device.

3. A device for raising or cultivating cells in a container-like receptacle (1) which comprises
a base; and
at least one lid,
wherein the at least one lid (3) is connected to the receptacle (1) in a pressure-tight manner, and the receptacle (1) or the at least one lid (3) is provided with at least one inlet bore (8) for one of the introduction and withdrawal of culture medium and oxygen, and
a magnetizable pressure disk (25) is arranged in the receptacle (1) and moved by a magnetizing means (24) in order to exert pressure internally on the cells (7).

4. The device as claimed in claim 3, wherein the pressure disk (25) is provided with holes (26).

5. The device as claimed in claim 3, wherein the pressure disk (25) has a grid or mesh structure.

6. The device as claimed in claim 3, wherein the cells (7) are arranged on a support structure (27a) which is acted upon by the pressure disk (25) from one or both sides.

7. A device for raising or cultivating cells in a container-like receptacle (1) which comprises
a base; and
at least one lid;
wherein the at least one lid (3) is connected to the receptacle (1) in a pressure-tight manner, and the receptacle (1) or the at least one lid (3) is provided with at least one inlet bore (8) for one of the introduction and withdrawal of a culture medium and oxygen,
a pressurizing means is located within a structure of the receptacle (1) for exerting fluid pressure on both the culture medium and the cells (7) being cultivated within the device so that a pressure load is exerted on the cells all round from outside.

8. The device as claimed in claim 7, wherein the pressurizing means is formed of expandable elements (28).

9. The device as claimed in claim 7, wherein the pressurizing means (17) is designed as a cylinder/piston unit.

10. The device as claimed in claim 7, wherein the pressurizing means (17) subjects an interior of the base receptacle (1) containing the cells (7) to alternating pressure loads.

11. The device as claimed in claim 7, wherein the pressurizing means includes a movable film, plate or membrane (31) arranged in the receptacle (1).

12. The device as claimed in claim 7, wherein the pressurizing means, which exerts the pressure load on the cells, is separate and independent of the culture medium.

13. The device as claimed in claim 7, wherein the pressurizing means exerts an alternating pressure load on the cells.

14. The device as claimed in claim 7, wherein the pressurizing means includes a movable film, plate or membrane (31)

arranged in the receptacle (1) and one of a hydraulic liquid and a gaseous medium is located on one side of the one of the movable film, plate or membrane (31) while the culture medium and the cells (7) are located on an opposite side of the one of the movable film, plate or membrane (31).

15. The device as claimed in claim 7, wherein the pressurizing means is one of a hydraulic liquid and a gaseous medium.

16. The device as claimed in claim 7, wherein the pressurizing means comprises one of a bag and a balloon and the culture medium and the cells (7) are located within one of the bag and the balloon.

17. The device as claimed in claim 14, wherein the culture medium is a gel.

* * * * *